US006802859B1

(12) United States Patent  
Pazienza et al.

(10) Patent No.: US 6,802,859 B1  
(45) Date of Patent: Oct. 12, 2004

(54) ENDOVASCULAR STENT-GRAFT WITH FLEXIBLE BIFURCATION

(75) Inventors: John Pazienza, Pompano Beach, FL (US); Mark Dallara, Tampa, FL (US); Bennie Gladdish, Weston, FL (US)

(73) Assignee: Endovascular Technologies, Inc., Santa Clara, CA (US)

(*) Notice: Subject to any disclaimer, the term of this patent is extended or adjusted under 35 U.S.C. 154(b) by 0 days.

(21) Appl. No.: 10/194,944

(22) Filed: Jul. 12, 2002

(Under 37 CFR 1.47)

(51) Int. Cl.$^7$ ................................................ A61F 2/06
(52) U.S. Cl. .................... 623/1.35; 623/623; 623/1.13
(58) Field of Search ............................ 623/1.12–1.22, 623/1.35

(56) References Cited

U.S. PATENT DOCUMENTS

| | | |
|---|---|---|
| 3,657,744 A | 4/1972 | Ersek |
| 4,140,126 A | 2/1979 | Choudhury |
| 4,562,596 A | 1/1986 | Kornberg |
| 4,787,899 A | 11/1988 | Lazarus |
| 5,064,435 A | 11/1991 | Porter |
| 5,489,295 A | 2/1996 | Piplani et al. |
| 5,562,724 A | 10/1996 | Vorwerk et al. |
| 5,575,817 A | 11/1996 | Martin |
| 5,609,627 A | 3/1997 | Goicoechea et al. |
| 5,628,788 A | 5/1997 | Pinchuk |
| 5,632,772 A | 5/1997 | Alcime et al. |
| 5,639,278 A | 6/1997 | Dereume et al. |
| 5,653,743 A | 8/1997 | Martin |
| 5,676,696 A | 10/1997 | Marcade |
| 5,683,449 A | 11/1997 | Marcade |
| 5,683,450 A | 11/1997 | Goicoechea et al. |
| 5,716,365 A | 2/1998 | Goicoechea et al. |
| 5,718,724 A | 2/1998 | Goicoechea et al. |
| 5,723,004 A | 3/1998 | Dereume et al. |
| 5,741,325 A | 4/1998 | Chaikof et al. |
| 5,755,769 A | 5/1998 | Richard et al. |
| 5,776,180 A | 7/1998 | Goicoechea et al. |
| 5,800,508 A | 9/1998 | Goicoechea et al. |
| 5,824,037 A | 10/1998 | Fogarty et al. |
| 5,824,042 A | 10/1998 | Lombardi et al. |
| 5,851,228 A * | 12/1998 | Pinheiro .................. 623/1.13 |
| 5,855,598 A | 1/1999 | Pinchuk |
| 5,916,263 A | 6/1999 | Goicoechea et al. |
| 5,938,696 A | 8/1999 | Goicoechea et al. |
| 5,993,481 A | 11/1999 | Marcade et al. |
| 6,015,431 A | 1/2000 | Thornton et al. |
| 6,051,020 A | 4/2000 | Goicoechea et al. |
| 6,099,558 A | 8/2000 | White et al. |
| 6,102,938 A | 8/2000 | Evans et al. |
| 6,117,167 A | 9/2000 | Goicoechea et al. |
| 6,123,722 A | 9/2000 | Fogarty et al. |
| 6,149,682 A | 11/2000 | Frid |
| 6,165,213 A | 12/2000 | Goicoechea et al. |
| 6,183,509 B1 * | 2/2001 | Dibie .................. 623/1.35 |
| 6,210,433 B1 * | 4/2001 | Larre .................. 623/1.15 |
| 6,302,906 B1 | 10/2001 | Goicoechea et al. |

OTHER PUBLICATIONS

U.S. 2002/0019659 A1, Goicoechea et al., filed Oct. 15, 2001.

(List continued on next page.)

Primary Examiner—Corrine McDermott  
Assistant Examiner—Hieu Phan  
(74) Attorney, Agent, or Firm—Fulwider Patton Lee & Utecht, LLP

(57) ABSTRACT

A modular bifurcated stent-graft implant having a trunk portion with graft material supported by a flexible stent lattice, the stent lattice extending from the proximal end of the trunk portion into each leg. The bifurcation of the trunk portion, which is supported by the stent lattice and graft material, is flexible such that the legs can move independently of each other both in and out of the plane of the midsection. The proximal end of the trunk portion is fully supported with one or more sealing stents. The legs and distal end of the stent-graft may be partially or fully supported 21 Claims, 6 Drawing Sheets

OTHER PUBLICATIONS

Chutter, et al., "Transfemoral Endovascular Aortic Graft Placement," Journal of Vascular Surgery, vol. 18, No. 2, Aug. 1993, pp. 185–197.

Parodi et al., "Transfemoral Intraluminal, Graft Implantation for Abdominal Aortic Aneurysms," Annals of Vascular Surgery, vol. 5, No. 6, 1991, pp. 491–499.

Criado et al., "Transluminal Recanalization, Angioplasty and Stenting in Endovascular Surgery: Techniques and Applications," From Greenhalgh, Vascular and Endovascular Surgical Techniques, 3rd Edition, 1994, pp. 49–70.

Marin et al., "Endoluminal Stented Graft Aorto–Bifemoral Reconstruction," from Greenhalgh, Vascular and Endovascular Surgical Techniques, 3.sup.rd Edition, 1994, pp. 100–104.

May et al., "Transluminal Placement of a Prosthetic Graft-Stent Device For Treatment of Subclavian Artery Aneurysm." Journal of Vascular Surgery, vol. 18, No. 6, Dec. 1993, pp. 1056–1059.

Chuter, T., "Bifurcated Endovascular Graft Insertion for Abdominal Aortic Aneurysm." from Greenhalgh, Vascular and Endovascular Surgical Techniques, 3.sup.rd. Edition, 1994, pp. 92–99.

Moore, W.S., "Transfemoral Endovascular Repair of Abdominal Aortic Aneurysm Using the Endovascular Graft System Device," for Greenhalgh, Vascular and Endovascular Surgical Techniques, 3.sup.rd. Edition, 1994, pp. 78–91.

* cited by examiner

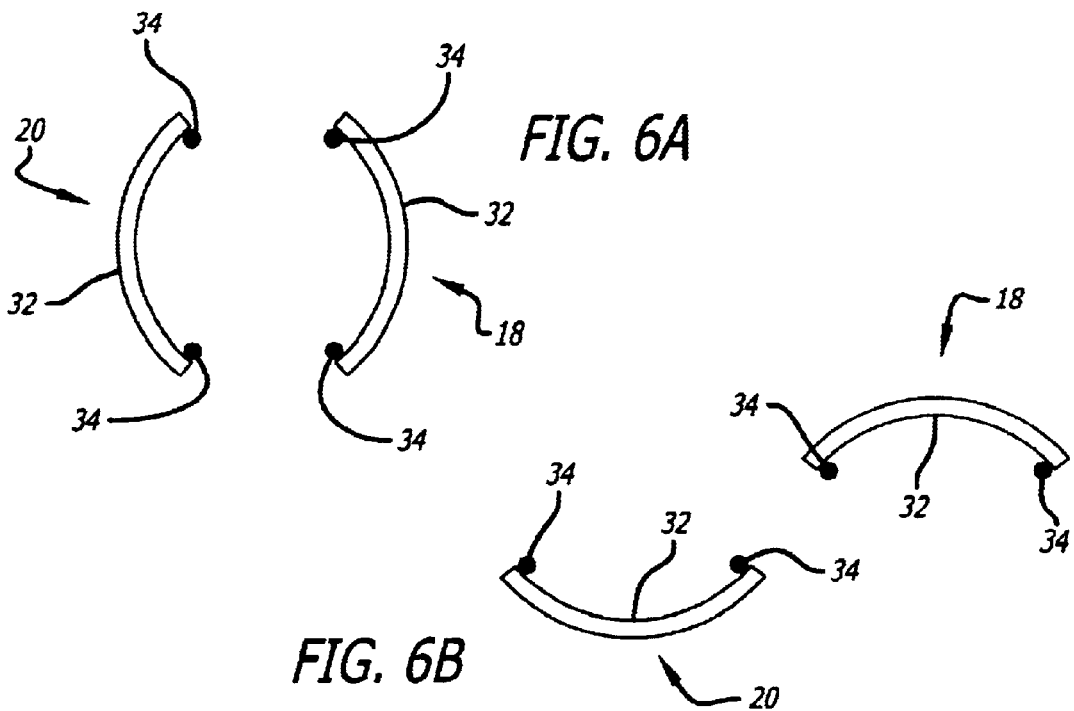
FIG. 6A
FIG. 6B
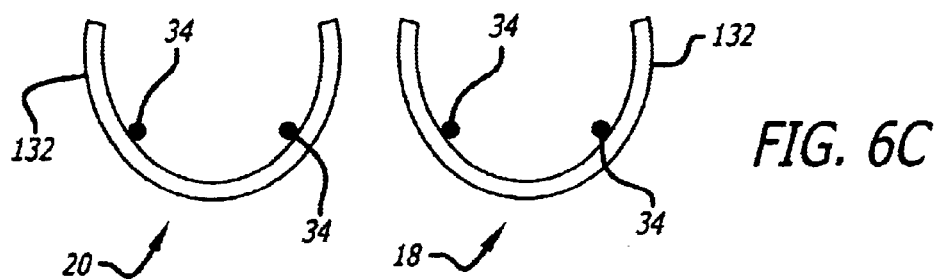
FIG. 6C
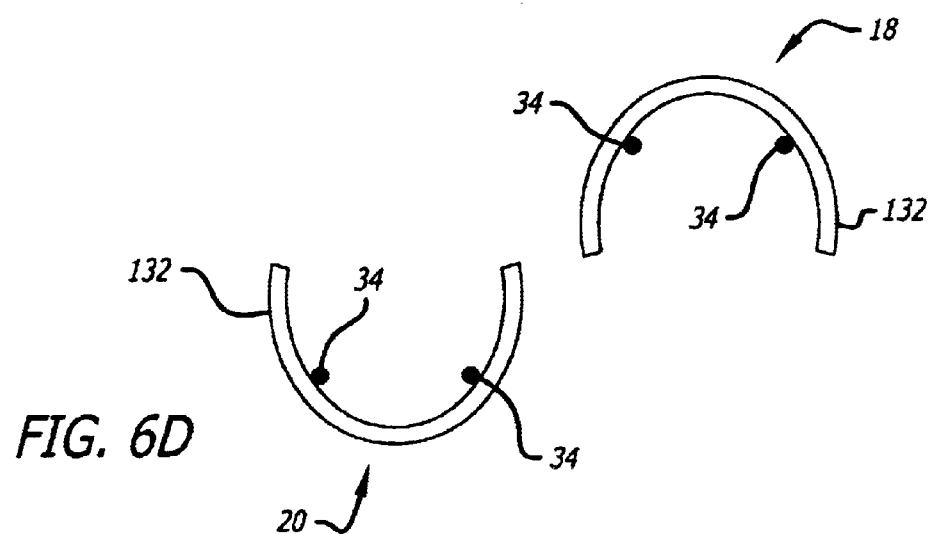
FIG. 6D

ENDOVASCULAR STENT-GRAFT WITH FLEXIBLE BIFURCATION

BACKGROUND OF THE INVENTION

This invention relates to intraluminal grafts for repairing defects in arteries and other lumens within the body. More particularly, the present invention relates to a bifurcated graft that is supported by a stent lattice and has legs that are independently flexible.

An abdominal aortic aneurysm is a sac caused by an abnormal dilation of the wall of the aorta as it passes through the abdomen. The aorta is the main artery of the body, supplying blood to various organs and parts of the body. It arises from the left ventricle of the heart, passes upward, bends over and passes down through the thorax and through the abdomen, and finally divides into the two iliac arteries which supply blood to the pelvis and lower extremities. The aneurysm ordinarily occurs in the portion of the aorta below the kidneys. When left untreated, the aneurysm will eventually cause the sac to rupture with ensuing fatal hemorrhaging in a very short time. The repair of abdominal aortic aneurysms has typically required major abdominal surgery in which the diseased and aneurysmal segment of the aorta is removed and replaced with a prosthetic device, such as a synthetic graft.

As with all major surgeries, there are many disadvantages to the foregoing surgical technique, the foremost of which is the high mortality and morbidity rate associated with surgical intervention of this magnitude. Other disadvantages of conventional surgical repair include the extensive recovery period associated with such surgery; difficulties in suturing the graft to the aorta; the loss of the existing thrombosis to support and reinforce the graft; the unsuitability of the surgery for many patients, particularly older patients exhibiting co-morbid conditions; and the problems associated with performing the surgical procedure on an emergency basis after the aneurysm has already ruptured.

In view of the foregoing disadvantages of conventional surgical repair techniques, techniques have been developed for repairing abdominal aortic aneurysms by intraluminally delivering an aortic graft to the aneurysm site through the use of a catheter based delivery system, and securing the graft within the aorta using an expandable stent. Since the first documented clinical application of this technique was reported, the technique has gained more widespread recognition and is being used more commonly. As vascular surgeons have become more experienced with this endovascular technique, however, certain problems have been encountered.

One of the biggest problems has been the kinking and/or twisting of the graft both during and after the graft has been implanted due to the often extreme tortuosity of the vessels adjacent to the aneurysm. A flexible stent-graft is required to accommodate the various bends in the vessels without kinking or twisting.

Endovascular repair of the abdominal aortic aneurysm (AAA) using a stent/graft prosthesis that is assembled in-situ is gaining acceptance due, in part, to the added flexibility that can be gained by providing limb portions that are not attached to the trunk portion. However, such modular stent-grafts can embody several disadvantages. There can be an increased risk of leakage in the area of the trunk portion where the limb portions are attached due to an inadequate seal between the limb portion and trunk portion or by the bending of the limb portion as it conforms to the patient's vasculature. Additionally, there can be a lack of support in the area of the bifurcation.

Therefore, there exists a need for an unibody or a modular bifurcated graft which provides a trunk portion having sufficient flexibility and support in the area of the bifurcation to allow the limb portions to bend in conformance to the patient's vasculature without the associated risk of leakage. The present invention addresses these and other needs.

SUMMARY OF THE INVENTION

Briefly and in general terms, the present invention is embodied in a bifurcated graft having a trunk portion with a flexible bifurcation that allows the leg portions to flex independently. Aspects of the present invention are applicable to both unibody and modular graft devices. In modular graft devices, the flexible bifurcation facilitates the attachment of limb portions which bend to conform to the patient's vasculature.

In one aspect of the invention, a flexible bifurcation is produced by combining a flexible Nitinol stent lattice with a woven bifurcated graft The flexible bifurcation allows each leg to bend in a wide and independent range of motion both in and out of the plane of the trunk.

In another aspect of the invention, a stent lattice is provided which is continuous throughout the trunk portion and extends into each leg. Since the stent lattice is continuous, additional support is provided in the area of the bifurcation. Furthermore, the presence of the stent lattice in each leg provides additional support for the limb portions and inhibits substantial kinking of the graft material when the limb portions bend upon being positioned within branch vessels. Moreover, the stent lattice provides column support for the graft to resist migration and help prevent drifting of the top of the graft during deployment.

The stent lattice may extend partially or completely around the circumference of each leg. Additional support rings, either partial of full, may be provided at the distal end of each leg in order to more securely attach a limb portion to the trunk portion.

Other features and advantages of the present invention will become apparent from the following detailed description taken in conjunction with the accompanying drawings, which illustrate, by way of example, the principles of the invention.

BRIEF DESCRIPTION OF THE DRAWINGS

FIG. 6A is view of the trunk portion shown in FIG. 1 from the distal end with the leg support rings and distal support rings in the same plane and the graft material not shown;

FIG. 6B is view of the trunk portion shown in FIG. 1 from the distal end with the leg support rings and distal support rings in different planes and the graft material not shown;

FIG. 6C is view of the stent lattice shown in FIG. 3 from the distal end with the leg support rings and distal support rings in the same plane; and FIG. 6D is view of the stent lattice shown in FIG. 3 from the distal end with the leg support rings and distal support rings in different-planes.

DETAILED DESCRIPTION OF THE PREFERRED EMBODIMENTS

As shown in the exemplary drawings and for purposes of illustration, the invention is embodied in a prosthetic bifurcated graft implant having a trunk portion that is supported by a flexible metal stent lattice covered by graft material. Each leg of the trunk portion is independently flexible both in and out of the plane of the trunk.

Figure 1:
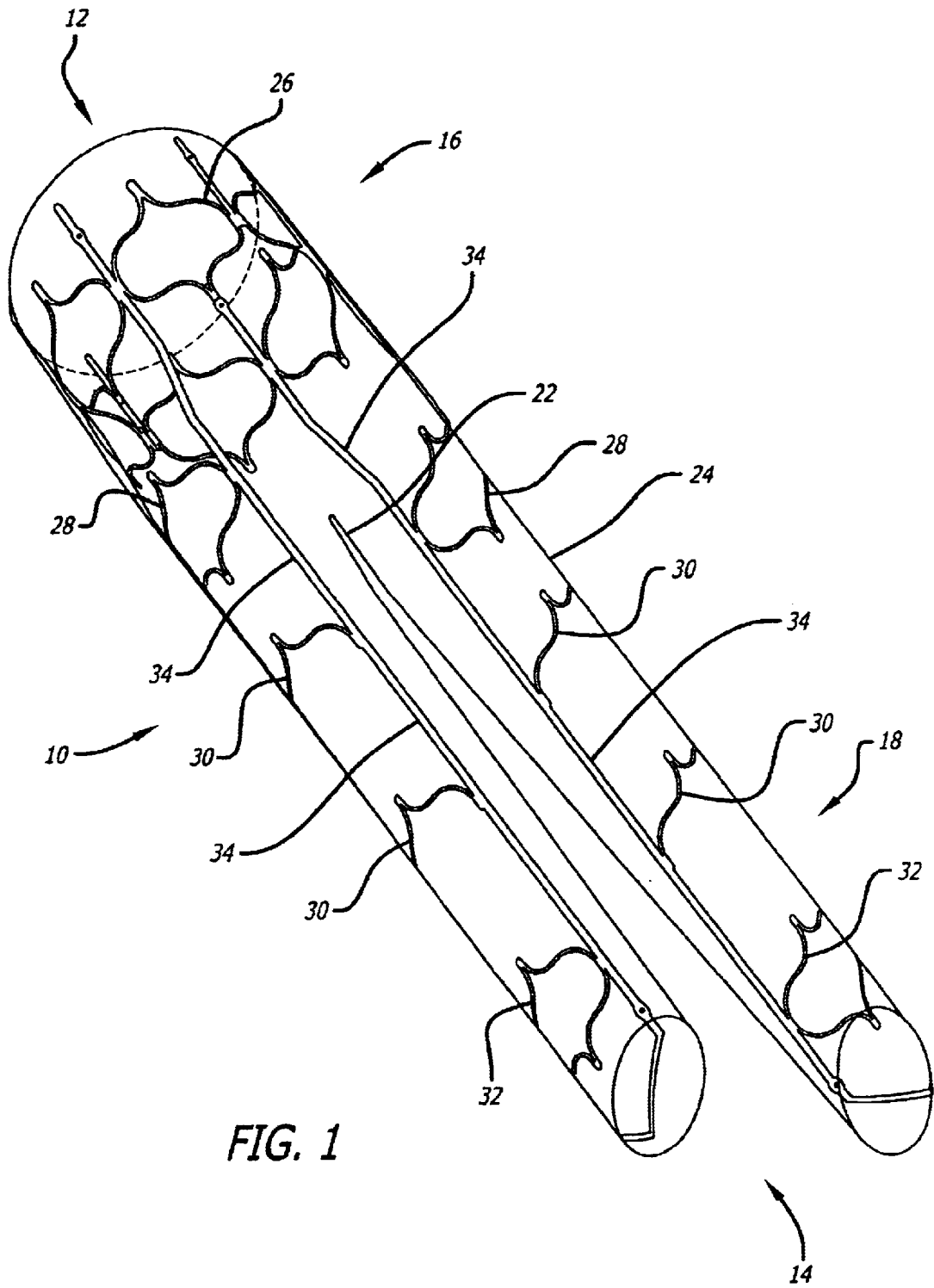
FIG. 1 is a semi-perspective view of a bifurcated trunk portion of the present invention, depicting a stent lattice and showing an outline of the graft material.

Referring to FIG. 1, a trunk portion 10 of an endovascular graft of the present invention is shown. The trunk portion 10 is defined by a proximal end 12, a distal end 14, a midsection 16, a contra-lateral leg 18, an ipsi-lateral leg 20, and a bifurcation 22. The graft material 24 is supported by a flexible Nitinol stent lattice and is sized such that the device extends from a main vessel to vessels branching therefrom. The stent lattice has a proximal sealing stent 26, bifurcation support stent rings 28, leg support stent rings 30, and distal support stent rings 32, each attached to longitudinal support struts 34 which extend from the proximal end 12 to the distal end 14. It is contemplated that the stent lattice can be interior or exterior the graft material and may extend down one or both legs. The stent lattice and graft material 24 form ipsi-lateral and contra-lateral docking sections into which limb portions are inserted (not shown) to form the multi-piece bifurcated graft implant using methods known in the art.

The proximal sealing stent 26, having full cells extending 360° about the circumference of the stent lattice, enables the midsection 16 of stent-graft 10 to be implanted in the vasculature of a patient above the aneurysm with the legs 18, 20 extending into the aneurysm sac. The longitudinal stent struts 34 provide longitudinal support for the entire length of the trunk portion 10 while allowing the trunk portion 10 to be flexible enough to conform to the various bends of the patient's vasculature without kinking closed or substantially closed so as to impede blood flow and possibly thromboses The bifurcation support stent rings 28 provide additional axial and longitudinal support in the bifurcation area 22. The leg support stent rings 30 provide additional longitudinal support along the entire length of each leg 18, 20 and axial and circumferential support for the limb portions (not shown. The distal support stent rings 32 provide additional circumferential and longitudinal support for the distal end 14 of each leg 18, 20 when a limb portion is inserted therein (not shown).

It is contemplated that additional proximal sealing stents 26, longitudinal stent struts 34, bifurcation support stent rings 28, leg support stent rings 30, and distal support stent rings 32 may be provided as desired. It is further contemplated that the bifurcation support stent rings 28, leg support stent rings 30, and distal support stent rings 32 may have full, half, or quarter cells that extend partially or 360° around the circumference of the stent lattice. Alternately, it is contemplated that the leg support stent rings 30 may be eliminated.

Figure 2A:
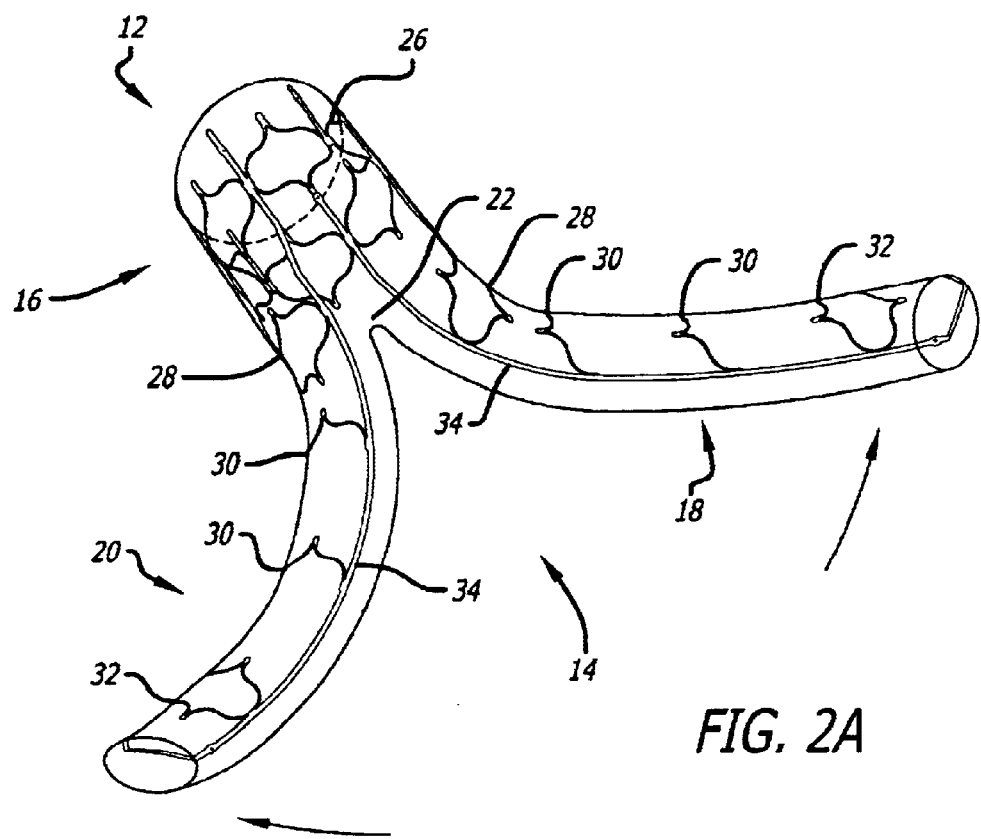
FIG. 2A is a view showing the bifurcated trunk portion of FIG. 1 with the legs bent in the same plane as the midsection.
Figure 2B:
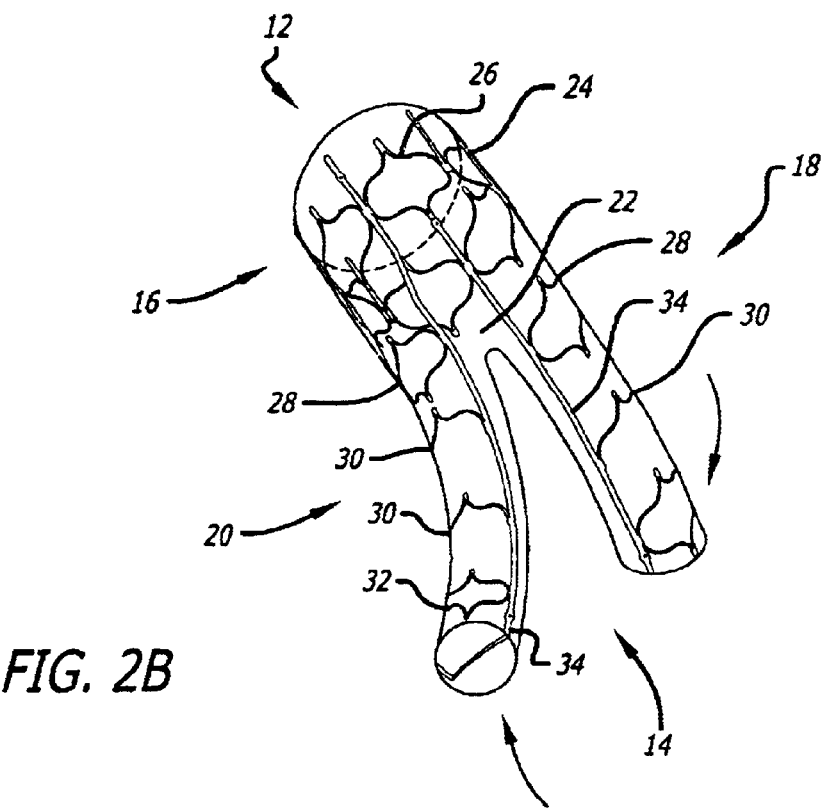
FIG. 2B is a view showing the bifurcated trunk portion of FIG. 1 with the legs bent in the plane 90° to that of the midsection.

As shown in FIGS. 2A and 2B, the bifurcation area 22 of the trunk portion 10 formed by graft material 24 allows the legs 18, 20 to independently bend both in a longitudinal plane sectioning the midsection 16 and leg sections 16, 18, 20 and in planes transverse and 90° thereto. The flexibility of the bifurcation area 22 is provided by the combination of the stent lattice and graft material 24 fabric.

Figure 3:
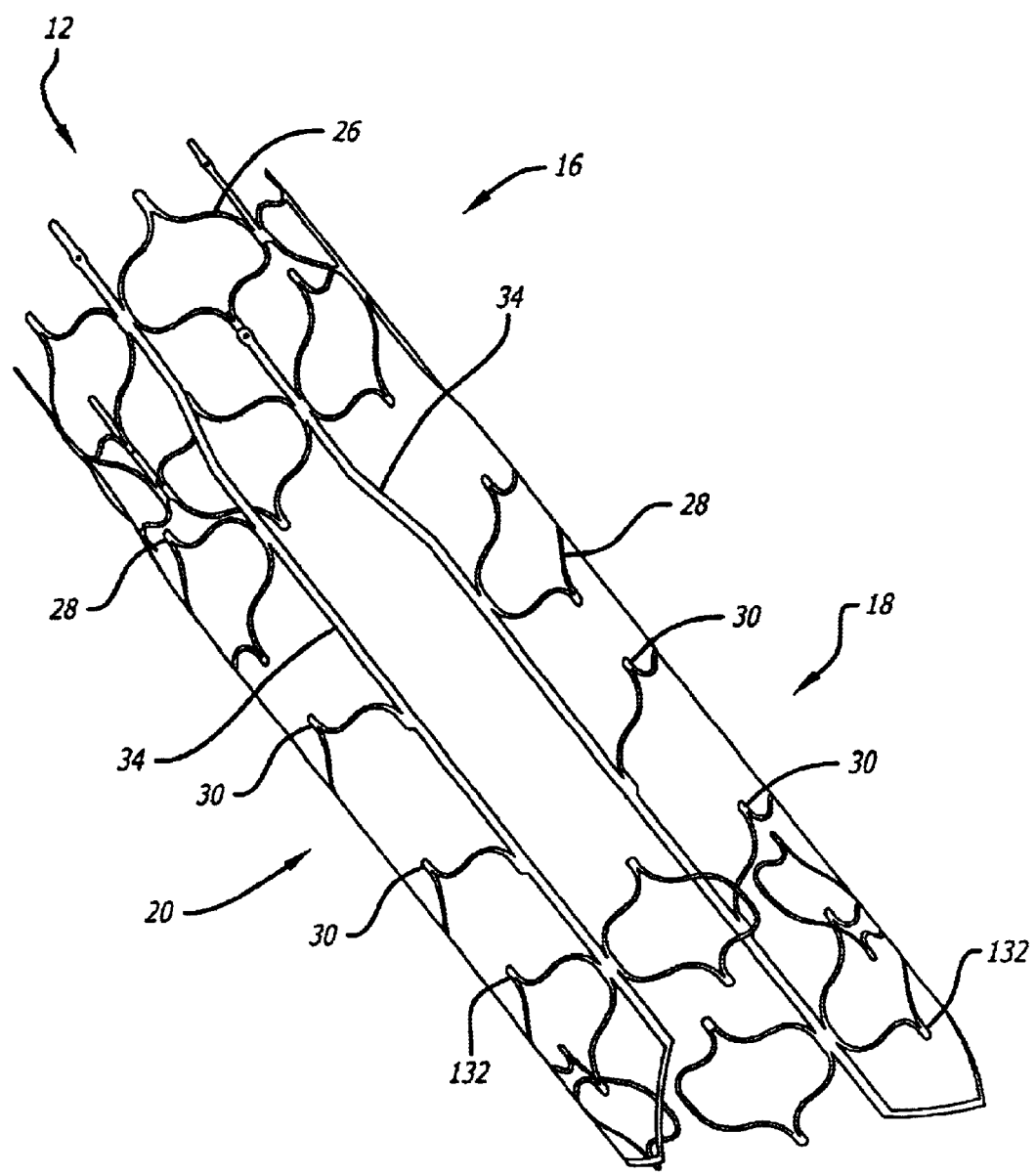
FIG. 3 is a perspective view of a bifurcated trunk portion stent lattice of the present invention with a partial support ring at the distal end of each leg.
Figure 4:
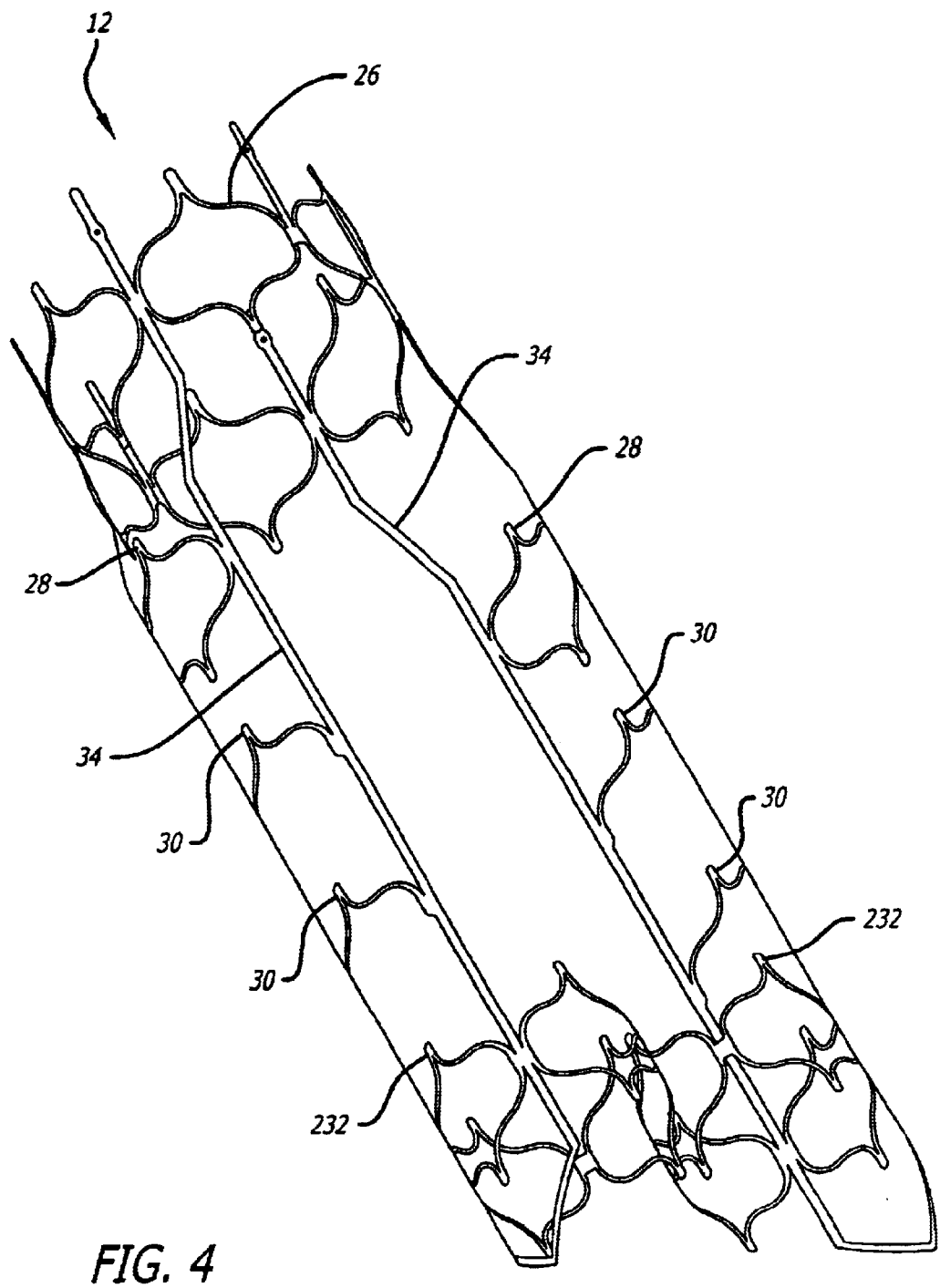
FIG. 4 is a perspective view of a bifurcated trunk portion stent lattice of the present invention with a full support ring at the distal end of each leg.

Referring to FIG. 3, an embodiment of a stent lattice of a trunk portion 10 of the present invention is shown that has distal support rings 132 that extend halfway around the circumference of the distal end 14 of each leg 18, 20. Referring to FIG. 4, an embodiment of a stent lattice of a trunk portion 10 of the present invention is shown that has distal support rings 232 that extend 360° around the circumference of the distal end 14 of each leg 18, 20. Although not provided in the embodiments of FIGS. 3 and 4, it is contemplated that additional longitudinal stent struts 34 may be provided for increased support of the midsection 16 and legs 18, 20.

Figure 5:
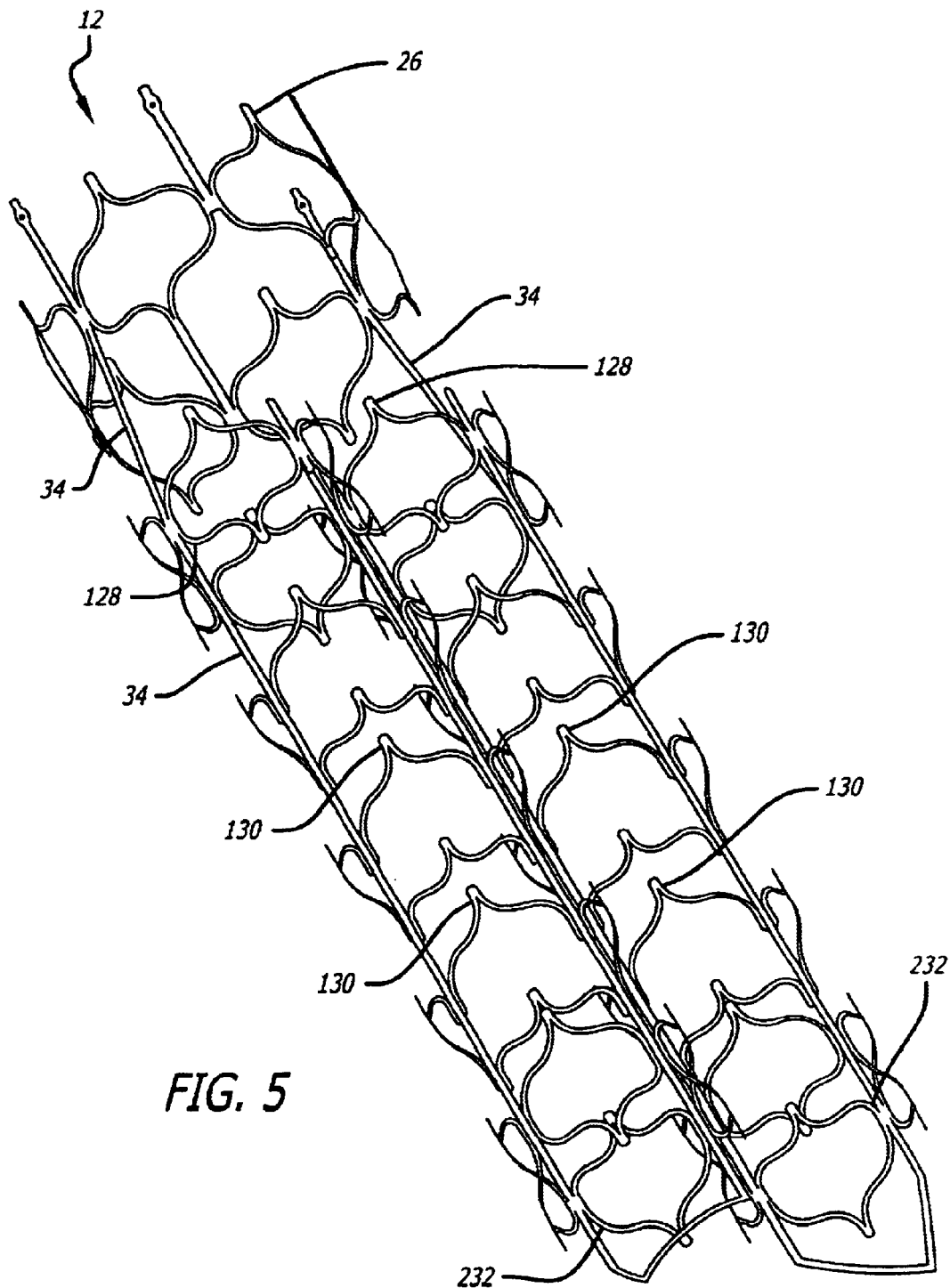
FIG. 5 is a perspective view of a bifurcated trunk portion stent lattice of the present invention that extends 360° about the circumference of the entire length of each leg.

Referring to FIG. 5, an embodiment of a stent lattice of a trunk portion 10 of the present invention is shown that has bifurcation support rings 128, leg support rings 130, and distal support rings 232 that extend 360° around the circumference of the distal end 14 of each leg 18, 20.

It is contemplated that the portion of the stent lattice that extends into each leg 18, 20 may be offset such that the leg support stent rings 30 and distal support rings 32 of each leg 18, 20 lie in different planes, as shown in FIGS. 6A–D. Offsetting the leg support rings 30 and distal support rings 32, particularly when they do not extend 360° about the circumference of the legs 18, 20, minimizes the amount of material in any given cross-section and further facilitates packing the trunk portion 10 for delivery.

While several particular forms of the invention have been illustrated and described, it will be apparent that various modifications can be made without departing from the spirit and scope of the invention. Accordingly, it is not intended that the invention be limited, except by the appended claims.

What is claimed is:

1. A bifurcated endoluminal prosthesis for repairing vasculature including a main vessel and two branch vessels, comprising:

a trunk portion having a proximal end, a midsection, two leg sections with distal ends, and a bifurcation area; and a self-expanding flexible stent structure extending from the proximal end into at least one of the leg sections and including longitudinal struts that provide longitudinal support from the proximal end of the trunk section to the distal end of the leg sections and stent cells attached to the longitudinal struts that provide at least partial axial and circumferential support for the midsection, leg sections and bifurcation area;

wherein the leg sections may bend independently from each other in directions transverse to the midsection and wherein each of the leg sections provides a docking area into which a limb portion may be inserted further comprises support stent cells at the distal end.

2. The prosthesis of claim 1, wherein the trunk portion further comprises sealing stent cells at the proximal end.

3. The prosthesis of claim 2, wherein the sealing stent cells comprise full cells extending circumferentially 360° around the proximal end.

4. The prosthesis of claim 1, wherein the support stent cells comprise full cells.

5. The prosthesis of claim 1, wherein the support stent cells comprise half cells.

6. The prosthesis of claim 1, wherein the support stent cells comprise quarter cells.

7. The graft of claim 1, wherein the support stent cells extend less than 360° around the circumference of the distal end.

8. The graft of claim 1, wherein the support stent cells comprise full cells extending 360° around the circumference of the distal end.

9. The prosthesis of claim 1, wherein the bifurcation area further comprises support stent cells.

10. The prosthesis of claim 9, wherein the support stent cells comprise full cells.

11. The prosthesis of claim 9, wherein the support stent cells comprise half cells.

12. The graft of claim 11, wherein the support stent cells comprise full cells extending 360° around the circumference of the leg section.

13. The prosthesis of claim 9, wherein the support stent cells comprise quarter cells.

14. The graft of claim 9, wherein the support stent cells extend less than 360° around the circumference of the bifurcation area.

15. The graft of claim 9, wherein the support stent cells comprise full cells extending 360° around the circumference of the bifurcation area.

16. The prosthesis of claim 1, wherein each leg section further comprises support stent cells between the bifurcation area and the distal end.

17. The prosthesis of claim 16, wherein the support stent cells comprise full cells.

18. The prosthesis of claim 16, wherein the support stent cells comprise half cells.

19. The prosthesis of claim 16, wherein the support stent cells comprise quarter cells.

20. The graft of claim 16, wherein the support stent cells extend axially less than 360° around the circumference of the leg section.

21. The graft of claim 1, wherein the stent structure comprises two or more longitudinal stent struts, at least one longitudinal stent strut extending into each leg section.

* * * * *

UNITED STATES PATENT AND TRADEMARK OFFICE
CERTIFICATE OF CORRECTION

PATENT NO. : 6,802,859 B1  
DATED : October 12, 2004  
INVENTOR(S) : John Pazienza, Mark Dallara and Bennie Glassish Page 1 of 1

It is certified that error appears in the above-identified patent and that said Letters Patent is hereby corrected as shown below:

Column 1,  
Line 6, delete "intraluninal" and insert -- intraluminal --.

Column 3,  
Line 12, delete "different-planes" and insert -- different planes --.  
Line 48, delete "thromboses" and insert -- thrombose. --.

Signed and Sealed this

Fifth Day of April, 2005

JON W. DUDAS  
*Director of the United States Patent and Trademark Office*